United States Patent [19]

Sleister

[11] Patent Number: 5,011,483
[45] Date of Patent: Apr. 30, 1991

[54] COMBINED ELECTROSURGERY AND LASER BEAM DELIVERY DEVICE

[76] Inventor: Dennis Sleister, 11 Briarbrook Dr., East Greenwich, R.I. 02818

[21] Appl. No.: 371,744

[22] Filed: Jun. 26, 1989

[51] Int. Cl.⁵ .............................................. A61B 17/32
[52] U.S. Cl. ........................................ 606/37; 606/13; 606/32; 606/41; 606/42
[58] Field of Search ..................... 606/2, 10–14, 606/32, 33, 37–42, 45–49; 128/303.1, 4, 6

[56] References Cited

U.S. PATENT DOCUMENTS

| | | | |
|---|---|---|---|
| 4,034,761 | 7/1977 | Prater et al. | 606/42 |
| 4,517,973 | 5/1985 | Sunago et al. | 606/16 |
| 4,534,347 | 8/1985 | Taylor | 606/33 |
| 4,597,380 | 7/1986 | Raif et al. | 606/14 X |
| 4,655,215 | 4/1987 | Pike | 606/42 |
| 4,688,569 | 8/1987 | Rabinowitz | 606/42 |
| 4,838,246 | 6/1989 | Hahn et al. | 128/6 |

FOREIGN PATENT DOCUMENTS

| | | | |
|---|---|---|---|
| 2901152 | 8/1979 | Fed. Rep. of Germany | 128/303.1 |
| 3642077 | 6/1988 | Fed. Rep. of Germany | 606/45 |
| 2513109 | 3/1983 | France | 128/303.1 |

Primary Examiner—Robert A. Hafer
Assistant Examiner—Kerry Owens
Attorney, Agent, or Firm—Kenyon & Kenyon

[57] ABSTRACT

An apparatus coupled to a laser delivery device comprising a housing having a laser waveguide for receiving a laser beam from the delivery device and for transmitting the laser beam to an area of medical treatment and a connection for receiving radio frequency electrical current and transmitting the current to an electrode for providing the current to the area of medical treatment. The apparatus combines the advantages of radio frequency electrosurgery techniques and laser surgery techniques in one device, offering the surgeon instant access to both techniques during surgery, as needed.

17 Claims, 2 Drawing Sheets

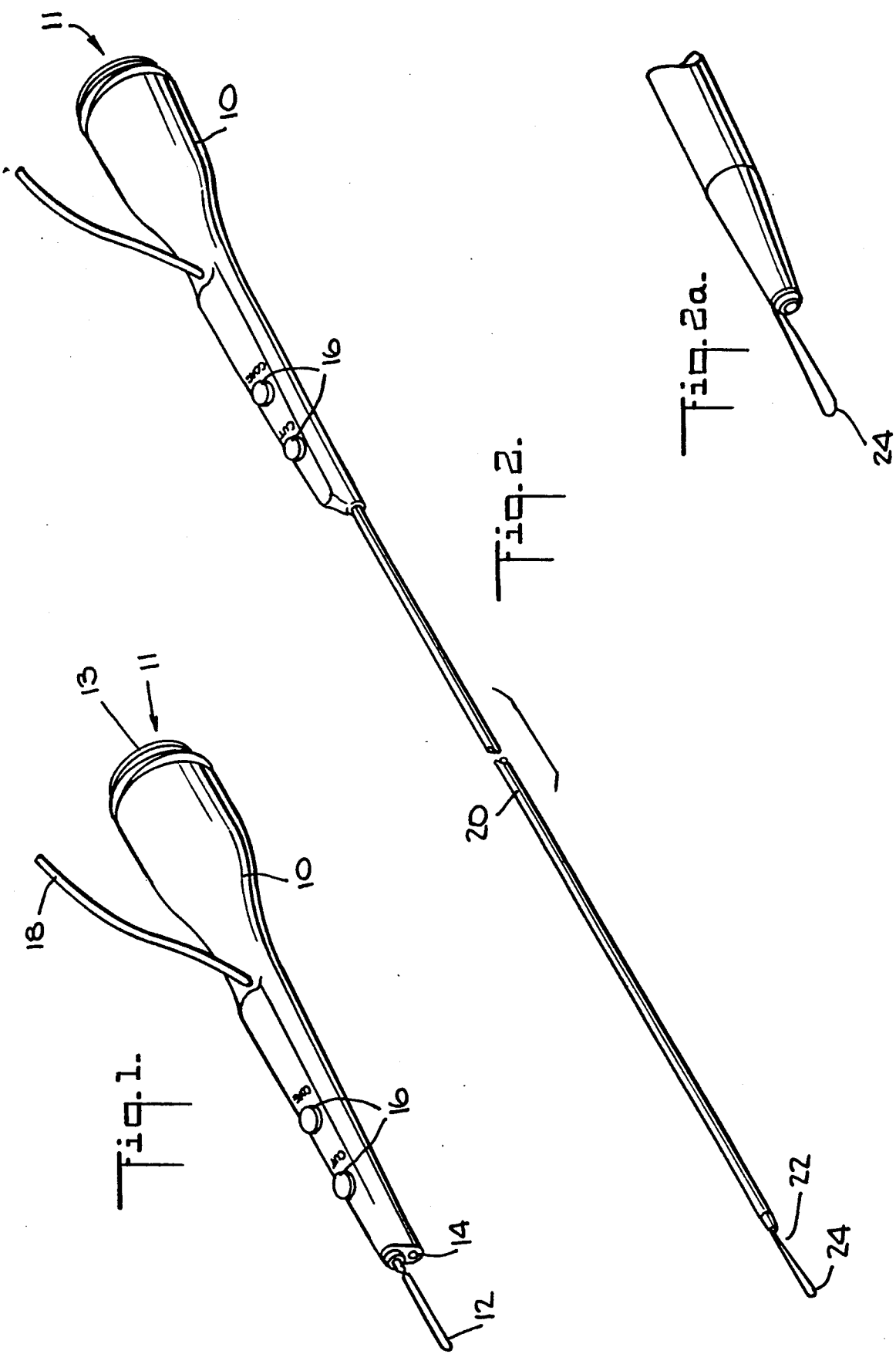

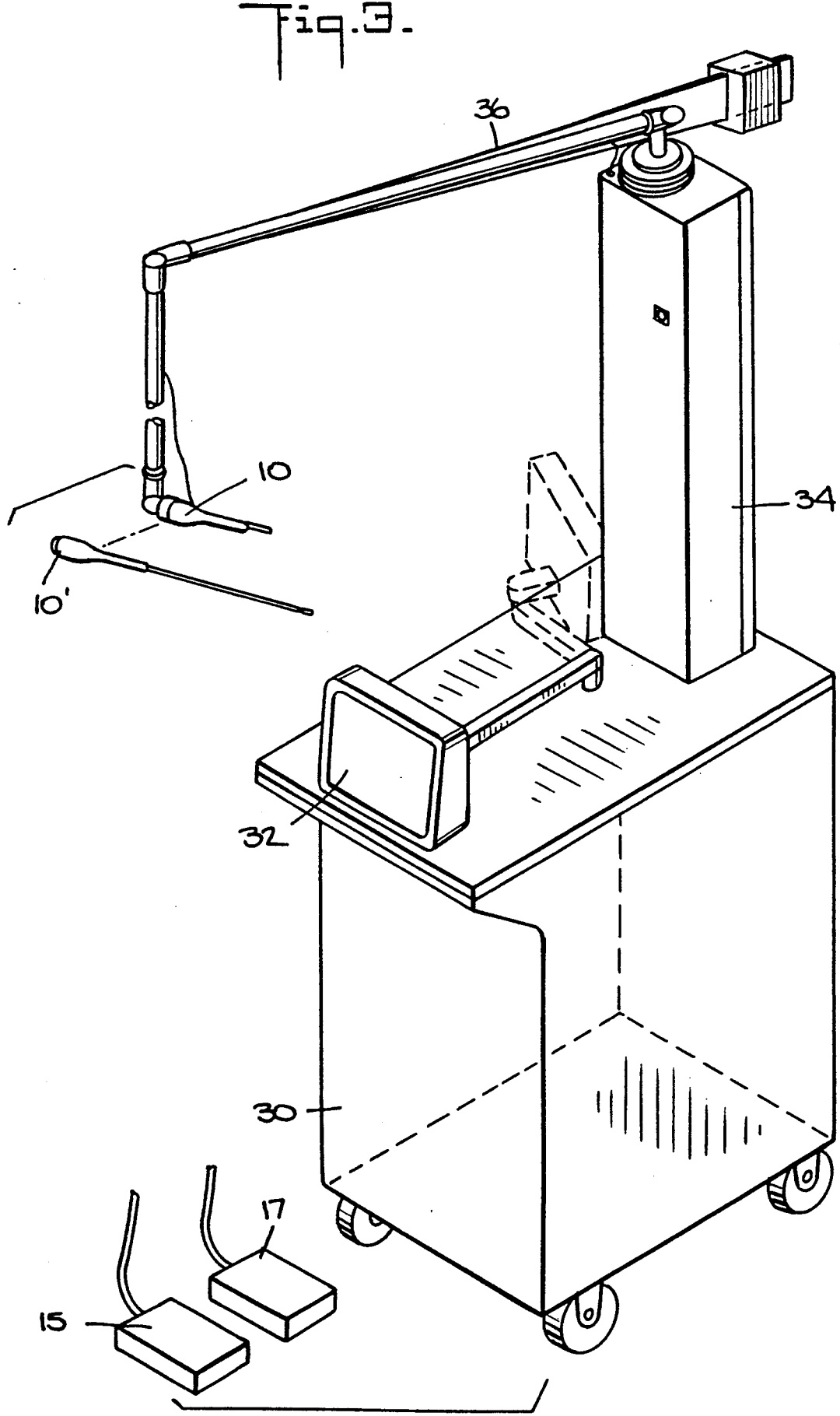

COMBINED ELECTROSURGERY AND LASER BEAM DELIVERY DEVICE

BACKGROUND OF THE INVENTION

The present invention relates to an apparatus that combines the advantages of electrosurgery and laser beam delivery techniques in a single device for use in surgery. The combined delivery device may be a handpiece at the end of a laser waveguide or an endoscopic delivery device. The electrosurgery R.F. generator for use with the device can be a stand-alone unit or built into the laser generating system, for example, a $CO_2$ laser system.

Electrosurgery has for decades been used to cut and coagulate tissue. Such systems are found in most operating rooms today. Electrosurgery units use radio frequency (R.F.) energy to create an A.C. arc which is applied to the tissue where the energy burns and coagulates the tissue. This results in reduced blood loss and is important in most surgical procedures. Currently, electrosurgery devices are separate instruments from other surgical devices, for example, laser beam delivery systems which may be used to cut tissue, for example, $CO_2$ laser systems. Although electrosurgical devices can cut tissue to some extent, they are very crude and destructive to the tissue.

$CO_2$ lasers, in contrast, provide a means for accurate cutting of tissue, but do not provide substantial coagulation effects.

During laser procedures with $CO_2$ lasers there are often problems with opened blood vessels that cannot be cauterized with a fan beam of the laser energy. This occurs with vessels larger than 0.5 mm.

Furthermore, there is some difficulty and time elapsed between the start of bleeding during surgery and the application of electrosurgery to stop the blood flow. The use of separate instruments for laser surgery and electrosurgery techniques therefore is not only inconvenient, but unacceptable during surgical techniques where speed is necessary. Furthermore, due to excessive bleeding, suction and clean-up must occur before the $CO_2$ laser can be used again.

Typical electrosurgery units comprise a radio frequency (R.F.) generator, an electrode (handpiece or pencil) and a cathode (a grounding pad). In the early 1970s, development of solid state electronic R.F. generators provided surgeons a safe power supply which did not pose the risk of burns that existing spark gap generators did. As a result of this development and recognition of the patient benefits of (1) shorter operating time and (2) reduced blood loss, surgeons rapidly adapted aggressive electrosurgery techniques. Today these techniques are used in nearly every hospital operating room procedure.

Electrosurgery cuts and coagulates with rather gross damage to tissue. In the late 1970s and early 1980s, the $CO_2$ laser began to be used in surgery because it could cut, coagulate or ablate tissue. It is an excellent cutting device but a poor coagulating device. In the 1980s, the YAG laser started to be used as a coagulating device which, however, does not cut well.

Applicant is aware of the following patents relating to electrosurgery and microwave instruments and techniques:

U.S. Pat. Nos.

4,688,569 to Rabinowitz
4,739,759 to Rexroth et al
4,562,838 to Walker
4,655,215 to Pike
4,534,347 to Taylor Applicant is also aware of the following laser beam delivery systems:

U.S. Pat. Nos.

4,638,800 to Michel
3,858,577 to Bass et al
4,583,526 to Ali
4,170,997 to Pinnow et al U.S. Pat. No. 3,357,433 to Fourestier et al discloses an endoscope and U.S. Pat. No. 4,765,322 to Charmillot et al discloses a method of treating neurovegetative disorders wherein electrically induced energy is applied to the brain. The energy may be electromagnetic energy including high frequency A.C. energy and laser energy.

None of the above references teach or suggest the usefulness of combining electrosurgery and laser surgery techniques in one instrument. Furthermore, to applicant's knowledge, no products are available which provide the advantages of electrosurgical and laser beam delivery techniques in one device.

SUMMARY OF THE INVENTION

Accordingly, it is an object of the present invention to provide an apparatus which combines the advantages of both electrosurgery and laser delivery techniques in one device, offering the surgeon instant access to both techniques during surgery, as needed.

It is furthermore an object of the present invention to provide such a device which can be used in medical/surgical applications, and particularly for those procedures requiring the ability to speedily change between laser cutting and electrosurgical cutting and/or cauterizing.

It is yet still a further object of the present invention to provide such a device which can be used in endoscopic applications.

It is furthermore an object of the present invention to provide an ergonomic laser beam/electrosurgery delivery device, which optionally may also have a detachable disposable or reusable handpiece.

The above and other objects of the present invention are achieved by an apparatus adapted to be coupled to a laser beam delivery device comprising a housing adapted to be coupled to the laser beam delivery device having means for receiving a laser beam from the delivery device and for transmitting the laser beam to an area of medical treatment and means disposed in the housing for receiving radio frequency electrical current and for transmitting the radio frequency electrical current to an applicator for providing the radio frequency electrical current to the area of medical treatment.

By combining both laser delivery techniques and electrosurgery R.F. techniques into an integrated system, a system is provided which permits both effective cutting and coagulating at the immediate election of the surgeon. Furthermore, the system of the present invention reduces bleeding time, increases the speed with which surgeons may perform medical operations and increases convenience during surgical procedures. Additionally, the present invention provides the surgeon with the ability to perform both gross cutting operations and fine accurate cutting operations, with the ability to coagulate as needed, at the surgeon's immediate election.

Other objects, features and advantages of the present invention will be apparent from the detailed description which follows.

BRIEF DESCRIPTION OF THE DRAWINGS

The invention will be described in greater detail in the following detailed description with reference to the drawings in which:

FIG. 1 shows a handpiece according to the invention which can be coupled to a laser beam delivery device, for example, an articulated arm laser beam delivery device;

FIG. 2 shows a combined electrosurgery and laser beam delivery device which is adapted to be used as an endoscopic delivery device;

FIG. 2a shows a detail of FIG. 2; and

FIG. 3 shows a typical laser beam delivery system wherein the invention is disposed at the end of an articulated arm for performing medical procedures.

DETAILED DESCRIPTION

With reference now to the drawings, one embodiment of the present invention comprises a handpiece which is adapted to be utilized at the end of a laser beam delivery system, for example, an articulated arm laser delivery device as shown in FIG. 3. Currently, laser handpieces are conically shaped, hollow metal devices through which the laser beam passes. Frequently, a removable metal tip is used on the distal end to give the surgeon an indication of the beam focal spot.

The integrated laser electrosurgery system handpiece of the present invention integrates an electrosurgery blade with a laser handpiece. The handpiece is referred to generally with 10 in FIG. 1. The length of the electrosurgery blade 12 can coincide with the focal spot of the laser beam from the laser output port 14. The laser or R.F. generator can be alternately activated by a suitable switch, such as foot switch 15 shown in FIG. 3. A foot switch can also be used to select the mode of electrosurgery, i.e., cut or coagulate, or suitable switches 16 on the handpiece can be provided, as shown in FIGS. 1 and 2. The electrosurgery electrode 12 and/or activator switch can either be part of the handpiece, as shown in FIGS. 1 and 2 or separate attachable pieces. A single electrosurgery blade can be used for monopolar R.F. energy delivery or two blades can be used for bipolar delivery. The wires 18 from the electrode 12 and/or switches 16 can go to an integrated control system which allows only delivery of either R.F. energy to coagulate or laser energy and/or R.F. energy to cut. Only one form of energy, i.e., laser or R.F., should be delivered at a time. The electrosurgery R.F. generator and laser should be integrated so that in the cut mode, only one system is available at a time.

The electrosurgery unit and laser may be integrated into one physical device or may be separate units. They are activated such that only one system is available at a time. The control and delivery wires 18 for the electrosurgery electrode and switches can run separately to the electrosurgery power supply, or they may be part of the articulated arm such that the connection would be made to the handpiece through the arm. Integrated delivery of R.F. and laser energy can also be performed in the fiber optic delivery of laser energy. R.F. conductive lines can parallel the fiber optic line to provide either an R.F. cutting or coagulation capability based on the type of laser used.

FIG. 1 shows one configuration of the handpiece. In this form, the handpiece may be made of plastic or metal, incorporating the functions and features of both the laser handpiece and electrosurgery pencil into a single ergonomic unit. The handpiece may be disposable. The handpiece has a laser beam input port 11 and suitable fastening means to couple to the laser delivery device, such as threads 13.

The unit may have switches 16 as shown for the standard cut/coagulate electrosurgery functions. Alternatively, the unit may be foot-switch actuated and therefore have control wires leading to the foot switch. Furthermore, bipolar electrosurgery may also be provided wherein the R.F. probe comprises two blades closely spaced as in forceps that can be brought together to initiate the discharge.

Another embodiment of the invention is shown in FIG. 2 wherein an endoscopic delivery system is provided. In this application, the laser beam would be delivered from the handpiece 10' down a long tube 20 either in free space or via a fiber optic or other form of waveguide to emerge on the site to be treated. This tube would be inserted into the lumen of an endoscope, for example, a laparoscope used for fertility procedures in female patients. The distal end 22 of the delivery tube may also have a loop of wire 24, as shown, particularly in detail in FIG. 2a, adjacent to the beam of laser light, that would be used for electrosurgery coagulation of bleeding tissue by either using switches on the beam launching handpiece 10' or a foot switch. Bipolar delivery of R.F. energy may also be used with this type of delivery system.

Such an endoscopic laser beam/electrosurgery delivery device can also be made disposable.

The concept of laser beam delivery in combination with electrosurgery is not necessarily limited to the above delivery devices but could also be used with other delivery devices, for example, a flexible waveguide delivery system.

FIG. 3 shows how the devices, as shown in FIGS. 1 and 2, are attached to a laser system. In the system shown in FIG. 3, the laser system may also include the electrosurgery R.F. generator or the R.F. generator may be a separate unit which supplies power to the electrosurgery/laser handpiece and is controlled via separate wires. As shown in FIG. 3, the laser system comprises the laser generation unit 30, a preferably movable and stowable control panel 32, a tower or laser head 34 to which an articulated arm 36 or flexible waveguide is attached and the articulated arm or waveguide itself to which the handpiece of the present invention is coupled. Foot switches 15 and 17 may be provided for control purposes, as discussed heretofore.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are, accordingly, to be regarded in an illustrative rather than in a restrictive sense.

What is claimed is:

1. Apparatus adapted to be coupled to a laser beam delivery device comprising:

a housing adapted to be coupled to the laser beam delivery device having means for receiving a laser beam from the delivery device and for transmitting the laser beam to an area of medical treatment;

means disposed in the housing for receiving radio frequency electrical current and for transmitting the radio frequency electrical current to an applicator for providing the radio frequency electrical current to the area of medical treatment; and a waveguide attached to said housing comprising means for delivering the laser beam from said housing to the area of medical treatment and further comprising means for delivering the radio frequency electrical current along the waveguide to the area of medical treatment, said waveguide being adapted to be inserted into the lumen of an endoscope for insertion into a living being, the applicator being disposed at a distal end of said endoscope for supplying the radio frequency electrical current to the area of medical treatment.

2. The apparatus recited in claim 1, further comprising switch means for selecting said laser beam or said radio frequency electrical current for delivery to the area of medical treatment.

3. The apparatus recited in claim 1, further comprising switch means for providing selected forms of said radio frequency electrical current to the area of medical treatment for enabling selection of a cutting function or a coagulation function with said radio frequency electrical current.

4. The apparatus recited in claim 1, wherein a means for producing radio frequency electrical current is disposed in said laser beam delivery device.

5. The apparatus recited in claim 1, wherein said laser beam delivery device comprises a laser beam generator and a laser waveguide for providing the laser beam to said housing.

6. The apparatus recited in claim 5, wherein said waveguide comprises an articulated arm laser waveguide.

7. The apparatus recited in claim 1, wherein the applicator comprises a wire loop.

8. The apparatus recited in claim 2, wherein said switch means comprises means for delivering alternatively said laser beam or said radio frequency electrical current to the area of medical treatment.

9. The apparatus recited in claim 1, wherein the applicator comprises an R.F. electrode.

10. The apparatus recited in claim 1, wherein said housing is removably detachable from said laser beam delivery device.

11. The apparatus recited in claim 10, wherein said housing is disposable.

12. The apparatus recited in claim 3, wherein said switch means is disposed in the housing.

13. The apparatus recited in claim 1, wherein said housing comprises plastic.

14. The apparatus recited in claim 1, wherein said housing comprises metal.

15. The apparatus recited in claim 8, wherein said switch means comprises a foot switch.

16. The apparatus recited in claim 3, wherein said switch means comprises a foot switch.

17. The apparatus recited in claim 1, wherein the laser beam comprises a laser beam generated by a $CO_2$ laser.

* * * * *